US007153475B2

(12) United States Patent
Hill et al.

(10) Patent No.: US 7,153,475 B2
(45) Date of Patent: Dec. 26, 2006

(54) AEROSOL PARTICLE ANALYZER FOR MEASURING THE AMOUNT OF ANALYTE IN AIRBORNE PARTICLES

(75) Inventors: Steven Clyde Hill, Silver Spring, MD (US); Richard Kounai Chang, Hamden, CT (US); Jean-Pierre Wolf, Lyons (FR)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 11/126,515

(22) Filed: May 9, 2005

(65) Prior Publication Data

US 2006/0252095 A1 Nov. 9, 2006

(51) Int. Cl.

| | |
|---|---|
| *B32B 5/02* | (2006.01) |
| *B32B 27/04* | (2006.01) |
| *B32B 27/12* | (2006.01) |
| *G01N 30/96* | (2006.01) |
| *C12M 1/34* | (2006.01) |

(52) U.S. Cl. ....................... 422/88; 422/83; 422/82.05; 422/82.08; 435/7.1; 435/283.1; 435/287.1; 435/287.2; 435/288.7; 436/35; 436/36; 436/149; 436/153; 436/172; 436/181; 356/36; 356/37; 356/300; 356/318; 356/335; 250/281; 250/282; 250/283; 250/288; 250/299

(58) Field of Classification Search .................. 436/35, 436/36, 149, 153, 172, 181; 422/83, 88, 422/82.05, 82.08; 435/7.1, 283.1–283.2, 435/288.7; 356/36, 37, 300, 318, 335; 250/281–283, 250/288, 299
See application file for complete search history.

(56) References Cited

U.S. PATENT DOCUMENTS

2005/0179893 A1* 8/2005 Hill ............................ 356/318

* cited by examiner

*Primary Examiner*—Long V. Le
*Assistant Examiner*—Jacqueline A. DiRamio
(74) *Attorney, Agent, or Firm*—A. David Spevack; Guy M. Miller; Stephen M. Bloor (57) ABSTRACT

Aerosol particle analyzer (APA) for measuring the amount of analyte in airborne particle is described. The APA uses an analysis liquid. In most embodiments, this analysis liquid is chosen so that when it is mixed with the particles, an optical property of the analysis liquid (AL) varies according to the amount of the analyte in the particles. Airborne particles are drawn into the instrument, and detected using optical methods such as light scattering or laser-induced fluorescence. When a particle of interest is detected, a charged droplet of the analysis liquid (CDAL) is ejected so that it collides with the detected particle and moves into a horizontally oriented linear quadrupole that is in an airtight container, except for small orifices to let the CDAL enter and exit. The CDAL is levitated in a high humidity environment so that it evaporates slowly, so that there is time for the reaction between the analyte, if any, and the CDAL can take place, and so that the optical property, typically fluorescence, can be measured. The amount of the analyte in the particle is determined from the measured fluorescence or other optical property. The particles collected into the CDAL can be sent on to other instruments for further analysis, especially to instruments that can analyze such small samples.

28 Claims, 5 Drawing Sheets

AEROSOL PARTICLE ANALYZER FOR MEASURING THE AMOUNT OF ANALYTE IN AIRBORNE PARTICLES

BACKGROUND OF THE INVENTION

1. Field of the Invention

This invention pertains generally to chemical analytical and immunological testing, and particularly to processes wherein samples are analyzed by using self-operated mechanisms or devices, and more particularly to processes wherein a continuously flowing stream of a sample or carrier fluid is formed and flows into and through analysis wherein the continuously flowing stream is segmented by alternately injecting a sample, reagent or any number of fluids into a common flow path.

2. Description of the Related Art

There is a need for improved methods for measuring analytes in airborne particles. For example, there is a need for devices that can quickly detect and identify the presence of harmful materials in airborne infectious agents such as bacteria, fungi, or viruses, which transmit many diseases of humans, other animals, or plants. Some airborne proteins and pollens cause allergies. Improved methods for characterizing aerosols would be useful for understanding atmospheric chemistry, including the sources, chemical reactions, and fates of atmospheric particles.

Here, "airborne particle" refers to both the solid particles and liquid droplets in an air sample. The analyte is the specific molecule, microorganism, or virus to be identified. For example, for biological warfare (BW) agents that are protein toxins, e.g., ricin, the toxin itself is the analyte. For BW agents that are bacteria or viruses, the analyte can be a molecule that is specific to the bacteria or virus to be detected, e.g., a protein or a DNA or RNA sequence. In this case the amount of the analyte is measured; if this amount is significantly above a noise threshold, the presence of the BW agent is inferred. For BW agents that are bacteria or viruses, the analyte can be the bacteria or virus itself.

Objectives for some types of instruments needed for detecting BW-agents or other analytes in airborne particles are: sensitivity, specificity, rapid response, continuous operation, little need for consumables, little need for operator time, and be able to separate and store particles for further analysis.

Investigators have worked for years to develop instruments and methods that are useful for detecting airborne BW agents, and other harmful airborne particles. Samples can be collected from air using a variety of different collectors, and the collected samples can be subjected to many different types of microbiological and biochemical analyses.

Some reasons why it is so difficult for the above objectives to be met simultaneously are as follows. The analyte may comprise a small fraction of the mass of a highly complex sample. Sensitivity and specificity requires the sample to be mixed with one or more liquids, termed here, "analysis liquids," where at least one of these liquids contains sensor molecules, also termed recognition molecules, that selectively bind to or interacts with the analyte. Example recognition molecules are antibodies and aptamers. Aptamers are DNA or RNA molecules that are selected for their ability to bind to the analyte. As a result of this binding of the recognition molecule to the analyte, some measurable property, e.g., fluorescence, must change according to the amount of analyte in the sample. That property is measured and the amount of analyte is inferred. Continuous operation requires continuous expenditure of consumables. Therefore, each measurement must require only a very small amount of consumables. In addition to the consumables used in analyzing the sample, consumables are typically expended in collecting particles from the air to be analyzed. If the particles are collected on filters or impacted on a surface, the filter or surface is a consumable unless it is cleaned, in which case whatever is used to clean it may be consumed. In typical analysis procedures for biochemical analytes in airborne particles, the airborne particles are collected into a liquid, which tends to evaporate as the sample is collected, especially if the air sample is warm and dry. Typically the consumable liquids, reagents, and/or filters, are sufficiently costly that it is too expensive to run instruments that identify biological molecules in air samples continuously for long periods of time.

The objectives of sensitivity and specificity, suggest choosing as analytes specific DNA sequences, and this approach may be applicable for some analytes. However, for a rapid response to spores, this approach is not feasible because 10's of minutes are required for the DNA from a spore to be extracted, amplified and detected. Also, this approach is not applicable to harmful substances that do not contain DNA or RNA, such as protein toxins.

A method to identify small amounts of analytes in airborne particles has been described, S. C. Hill, Aerosol Particle Analyzer for Measuring the Amount of Analyte in Airborne Particles, U.S. patent application Ser. No. 10/708, 191, filed Feb. 14, 2004 and herein incorporated by reference. That application described a method for collecting particles into levitated droplets of an analysis liquid in order to rapidly detect analytes in the particles, and stated that the droplets of the analysis liquid could be collected and further analyzed. That invention was aimed specifically at the detection of analytes in particles without having the particles come into contact with any surface, so that there would be no problem of cross contamination from sample to sample. That application described the detection of the analyte by using a homogeneous assay in droplets levitated in a linear quadrupole. Manipulating multiple droplets levitated in a linear quadrupole was described by S. Arnold, P. Hendrie and B. V. Bronk, U.S. Pat. No. 5,532,140, Method and Apparatus for Suspending Microparticles, herein incorporated by reference. The method requires levitating or otherwise controlling the motion of a charged droplet for a sufficient time for the oppositely charged particles to combine with it.

H. B. Lin and S. C. Hill, Aerosol Particle Analyzer for Measuring an Analyte in Airborne Particles, U.S. patent application Ser. No. 10/816,579, filed Mar. 26, 2004, described an apparatus for collection of particles into a small volume of an analysis liquid at the end of a capillary tube, and where an optical change in the volume of liquid on the end of the capillary tube is detected if the analyte was in the particles that combined with that volume of analysis liquid. In that application, the rate of the collection of the particles is enhanced by electrostatic forces between the particles and the charged volume of liquid at the end of the capillary.

S. C. Hill and H. B. Lin, Aerosol Into Liquid Collector for Depositing Particles from a Large Volume of Gas into a Small Volume of Liquid, submitted to US Patent Office, Nov. 19, 2004, describes a means of collecting airborne particles into a small volume of liquid held at the end of a capillary.

For the two methods mentioned above in which the particles are collected into droplets held on the end of a capillary, there is some concern that particles may stick to the sides of the capillary.

Another potential problem for the methods described above, as far as measurement of biological analytes is concerned, is that the particles are given an electric charge, so that they have a charge that is opposite to that of the droplets and are attracted to the droplets. However, there is a concern that the charging of the particles may modify the biological analytes in these particles so that they can no longer be specifically analyzed.

Another limitation is as follows. The above methods collect all of the particles, having sizes above some minimum size, into the droplets for analysis (although not all with the same collection efficiency). Therefore, if, in an air sample, there is a very large excess of particles that do not contain analyte, then either (i) each droplet that contains a particle with analyte also contains many other particles that do not contain analyte, and therefore the sensitivity of the analysis may be reduced because of nonspecific binding problems, or (ii) a relatively large number of droplets is required for the analysis if there is to be only one or a very few particles per droplet to minimize problems from nonspecific binding, and so more of the instrument must be devoted to handling these droplets and measuring the fluorescence that occurs in them, and more of the reagents must be used, although for many cases the net use of reagents may be sufficiently small.

SUMMARY OF THE INVENTION

In consideration of the problems detailed above and the limitations in the partial solutions thereto, an object of the present invention is to provide an improved aerosol particle analyzer (APA) for measuring the amount of analyte in airborne particles. In this invention the term "particles" includes both solid and liquid particles.

Another object of the present invention is to provide an APA that is sensitive to a small number of particles that contain the analyte in a large volume of air;

Yet another object of the present invention is to provide an APA that is specific for the analyte;

Yet a further object of the present invention is to provide an APA that has a rapid response, with no more than a short delay between the time the analyte aerosol enters the instrument and the time the instrument indicates that an analyte has been identified.

Yet another object of the present invention is to provide an APA that can run continuously.

Yet another object of the present invention is to provide an APA that has a low requirement for consumables.

Yet another object of the present invention is to provide an APA that does not require charging of the airborne particles.

Yet another object of the present invention is to provide an APA that can provide the particles, once analyzed, to the input port of another analyzer or storage system, so that the particles may be further analyzed and stored as desired.

Yet another object of the present invention is to provide an APA that is capable of collecting and analyzing the airborne particles that have specified optical scattering or emission features, but not collecting or analyzing those particles that lack these features.

Yet another object of the present invention is to provide an APA that has little need for operator time.

In order to attain the objectives described above, according to an aspect of the present invention, there is provided an aerosol particle analyzer for measuring the amount of an analyte in airborne particles in a gas such as the atmosphere. The main parts of this airborne particle analyzer are as follows.

An analysis liquid that has the following property: when the analysis liquid is mixed with particles, the fluorescence of the analysis liquid varies according to the amount of the analyte in the particles, so that the amount of analyte can be determined from measurements of the fluorescence. No wash steps or separation is allowed, that is, the analysis liquid used in this present invention must be suitable for a homogeneous assay. To achieve the objective of specificity, the analysis liquid typically requires molecules, such as aptamers, antibodies, nucleic acids, or phage-displayed epitopes, that are specific for the analyte. To help achieve the objective of sensitivity, the analysis liquid typically uses a reporter molecule such as a fluorophore that can be detected even in very low amounts.

A charged-droplet generator ejects a charged-droplet of the analysis liquid (CDAL) when signaled to do so. Because the CDAL is typically less than 200 micrometers in diameter, it is possible to eject CDAL at a rate of a few per second and still satisfy the objective of using only a small amount of consumables.

A particle-droplet-collision subsystem (PDCS) that includes an aerosol particle detector (APD). The PDCS is connected to a vacuum pump that draws the gas and particles into PDCS, then into the APD, and on through the region where particles detected can collide with a CDAL ejected by the charged droplet generator. If the APD detects a particle, it signals for the charged droplet generator to eject a CDAL so that it moves on a trajectory so as to collide with the detected particle. The CDAL, after it collides with the detected particle, continues moving in the direction it was ejected, and moves out of the PDCS and into the droplet analysis subsystem (DAS). The PDCS provides a way for particles to be collected from the air sample and to be mixed with the analysis liquid very efficiently, and without coming into contact with surfaces that may become contaminated and require cleaning or replacement. By so doing the PDCS satisfies the objectives of using only a small amount of consumables. Because the particles and analysis liquid do not come into contact with surfaces, there is less chance for interference and this low probability of interference helps contribute to the high sensitivity of the APA. It also provides a way to analyze only the particles that have some optical property of interest, so that if enough is known about the particles of interest, some of the potentially interfering particles may be ignored, and so the sample rate can be higher. For example, the APD can measure the particle size and its fluorescence spectrum, so that only particles having preselected sizes and/or having preselected fluorescence properties are caught by the CDAL. Also, this information about the size and fluorescence properties of the particle that combines with the CDAL can help in correcting for background signals or nonspecific binding of the aptamers or other recognition molecules to other materials in the particle collected, and so can contribute to the objective of high sensitivity. These measurements can be especially useful in cases where it is more probable that nonspecific reactions will occur between the analysis liquid and other molecules that are not the analyte. If such reactions result in changes in fluorescence that appear like those that occur with the analyte, then the sensitivity is reduced, or the false positive rate is increased.

A droplet analysis subsystem (DAS) that accepts the CDAL ejected by the PDCS, then levitates these CDAL for the time needed for the analyte to react with the analysis liquid and for the fluorescence to change if analyte is present, and it measures the fluorescence of the levitated CDAL so that the amount of analyte in the particle that combined with the CDAL can be determined. The DAS is substantially airtight, except for a small hole through which the CDAL is injected, and in some cases a small hole through which the CDAL may be ejected, so that water vapor leaks relatively slowly from the DAS so that the humidity in the DAS remains high, so that the CDAL evaporates slowly, so that there is sufficient time for the reaction between the analyte and the analysis liquid to take place and for the fluorescence to be measured, so that the amount of analyte in the particles can be determined. By holding the droplets so that the complete analysis of analyte in the particles is made using only the amount of analysis liquid in the CDAL, in some cases on the order of a nanoliter, the objective of using only a small amount of consumables is achieved.

By performing the complete analysis for each individual particle collected (each CDAL contains only one particle), problems with nonspecific binding of the analysis liquid to molecules that are not analyte are reduced. In this respect the APA is similar to a flow cytometer and shares the benefit of measuring the fluorescence signal from one particle at a time. If the fluorescence is measured from many particles at once, for example, from 1000 particles in a case where only one particle contains analyte, then even if there is a small amount of nonspecific binding to non-analytes, the fluorescence signal from the binding to non-analytes may overwhelm the fluorescence from the binding to the analyte, so that the binding to the analyte cannot be detected, and the sensitivity is reduced. The APA is a single particle detector, and so the fluorescence from the one particle that contains analyte is compared, individually, with the fluorescence from each of the 999 particles that do not contain analyte. Therefore APA satisfies the objectives of being sensitive to a small number of particles that contain the analyte in a large volume of air, and in being specific for the analyte.

Another component used in some embodiments of the APA is an aerosol particle charger that imparts a negative charge to each particle entering the PDCS so that the particle is attracted to the positively charged CDAL that is shot at it, so that the collection efficiency, especially for small particles, is increased. This charger can increase the sensitivity of the APA.

Another component used in some embodiments of the APA is an aerosol particle concentrator that concentrates particles in the air before they enter the charger. It can greatly increase the sensitivity of the APA.

The aforementioned features, objects, and advantages of this method over the prior art will become apparent to those skilled in the art from the following detailed description and accompanying drawings.

DETAILED DESCRIPTION OF THE PREFERRED EMBODIMENTS

Figure 1:
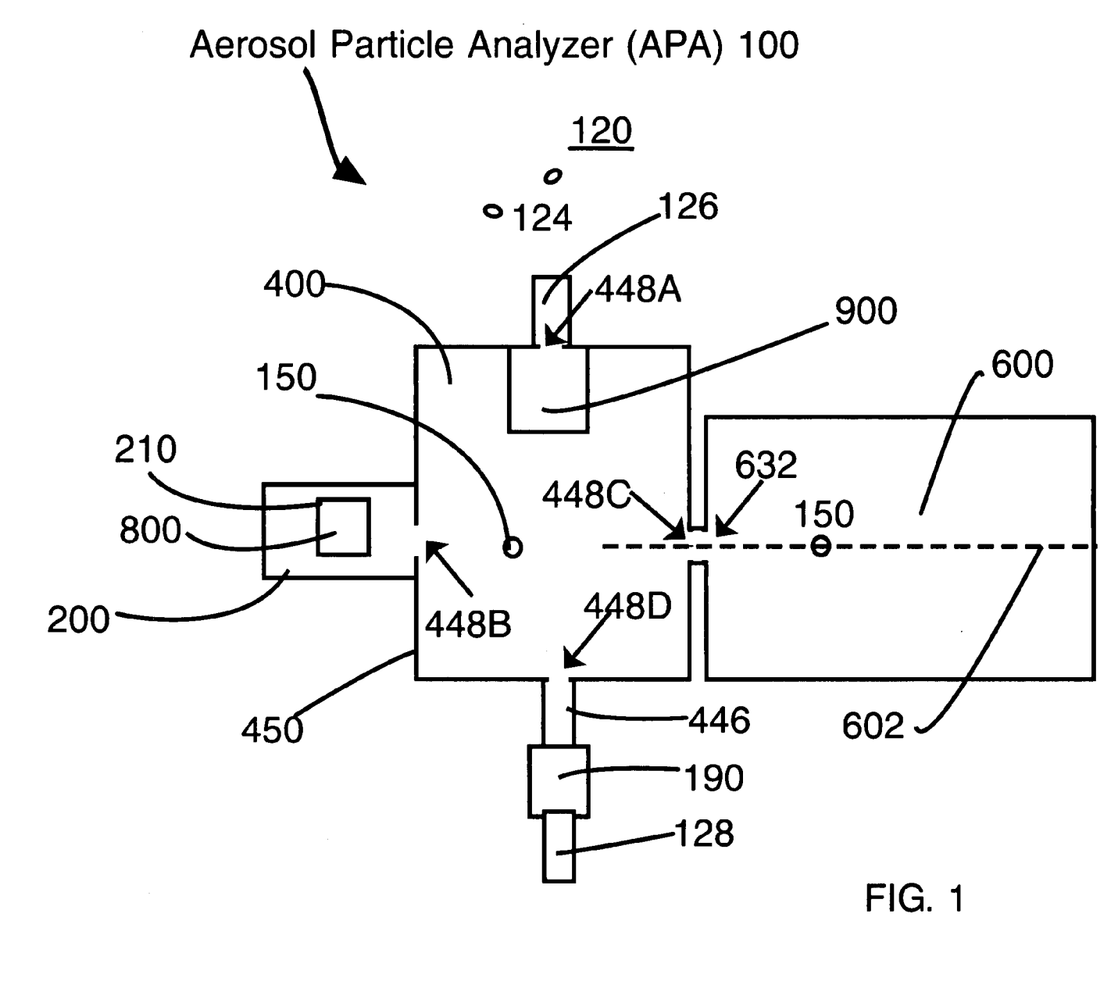
FIG. 1 illustrates schematically the APA.

Referring to FIG. 1, an aerosol particle analyzer (APA) 100 is immersed in a gas 120, such as the atmosphere, having particles 124 therein. Generally, the particles 124 include many types of particles 124, some of which may contain no analyte 80, and some of which may contain some amount of the analyte 80. The particles 124 may be liquid, solid, or a mixture of liquid and solid.

An analysis liquid 800 is in a reservoir 210 in the charged-droplet generator (CDG) 200. The analysis liquid 800 is chosen to have the following property: when the analysis liquid 800 is mixed with particles 124, the fluorescence of the analysis liquid 800 varies according to the amount of the analyte 80 in the particles 124, so that the amount of analyte can be determined from measurements of the fluorescence. No wash steps or separation is allowed, that is, the analysis liquid 800 used in this present invention must be suitable for a homogeneous assay.

The measurement of the analyte 80 in the particles 124 is accomplished as follows. The pump 190 draws gas 120 and particles 124 into the APA 100 through an induction port 126, then through the particle-droplet-collision subsystem (PDCS) 400, and then exhausts at least the gas 120 out of an output port 128. An aerosol-particle detector (APD) 900 in the PDCS 400 detects when a particle having certain optical characteristics passes through a predefined detection region in the APD 900. When the APD 900 detects such a particle, it signals to the CDG 200 to eject a charged-droplet-of-the-analysis-liquid (CDAL) 150 into the flow of gas 120 and particles 124 with a direction and velocity such that it: (a) enters the PDCS 400 on a trajectory such that it is likely to collide with the particle 124 detected by the APD 900, and (b) moves out of the PDCS 400 with a velocity and direction such it that moves into a droplet analysis system (DAS) 600 and is caught and held for analysis.

If one or more of the particle(s) 124 that mix with the CDAL 150 contain some analyte 80, the fluorescence of the CDAL 150 changes in accordance with the amount of the analyte 80, but this change is not instantaneous. In some cases the change may take minutes. For example, if the analyte 80 is inside a particle 124, time may be required to dissolve the analyte 80 so that it can be detected. In the DAS 600 the CDAL 150 is levitated for a time sufficient for the analyte 80 to react with the analysis liquid 800 to generate fluorescence, and then the fluorescence of the CDAL 150 is measured. The amount of the analyte 80 in the particles that collided with the CDAL 150 is determined from this measured fluorescence. This process of detecting a particle 124, ejecting a CDAL 150 to collide with this particle 124, and measuring the amount of analyte 80 in the levitated CDAL 150 in the DAS 600 is repeated for as long as desired, for example, days. A computer, controller, voltage sources and electronics subsystem (CCVSES) controls the timing of the generation of the CDAL 150, the motion of the CDAL 150 in the DAS 600, and the measurement of the fluorescence and the determination of the amount of analyte 80 from that measured fluorescence.

By using only a small amount of the analysis liquid 800 for each measurement, the APA 100 satisfies one objective of the APA 100. By keeping the CDAL 150 levitated from the time of generation of the CDAL 150 to the time of measurement of the fluorescence, the APA 100 avoids contact of the CDAL 150 with any surface, and thereby eliminates cross contamination and reduces the need for replacing expendable items, thereby satisfying another objective of the APA 100. By separating the PDCS 400, in which the gas 120 flowing past the CDAL 150 may have a very low humidity, from the DAS 600, which is airtight except for the inlet orifice to the DAS 632 through which COAL 150 from the PDCS 400 enters, the humidity in the DAS 600 can be kept high so that the CDAL 150 evaporates sufficiently slowly. Therefore, the reaction between the analyte 80 and the analysis liquid 800 has time to take place, and the amount of analyte 80 can be determined.

The PDCS 400 illustrated in FIG. 1 includes a PDCS-container 450 which is substantially airtight except for orifices 448: a particle-gas entrance orifice 448A, here used to receive particles 124 and gas 120; a CDAL entrance orifice 448B which receives CDAL 150 from the CDG 200; a PDCS-exit-orifice 448C through which CDAL 150 moves into the DAS 600; and a pump orifice 448D to remove the gas 120 that is drawn through the pipe 446 that connects to the pump 190.

Figure 2:
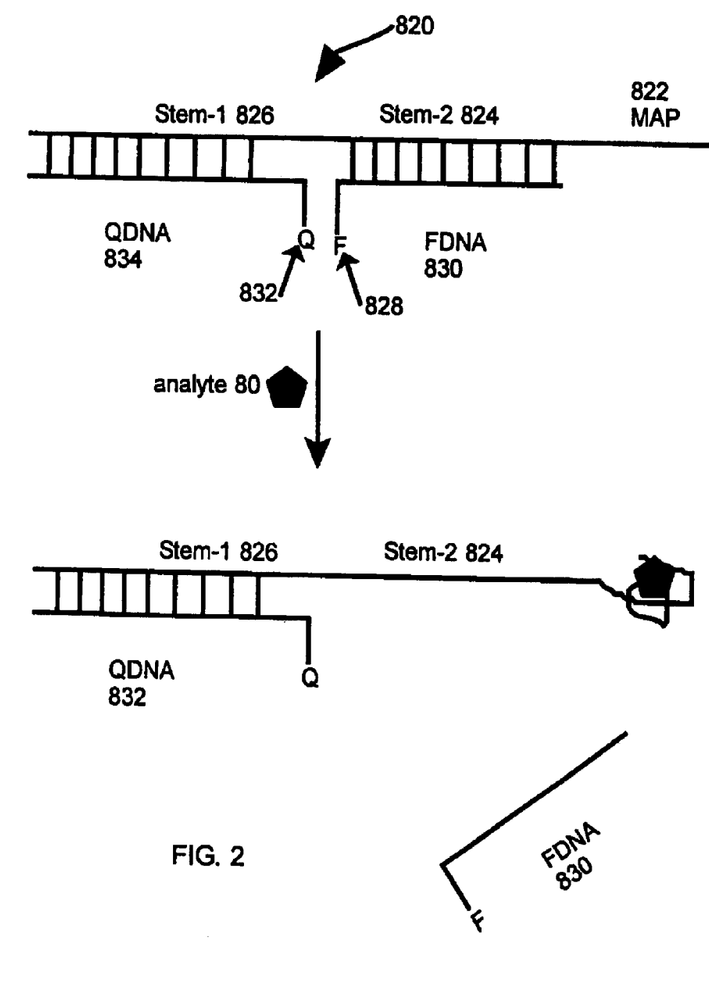
FIG. 2 illustrates schematically an embodiment of the reaction that takes place in the charged droplet of the analysis liquid (CDAL) when analyte is present in a particle that collided with the droplet; and, FIGS. 3A and 3B illustrates schematically the droplet analysis subsystem (DAS).

FIG. 2 illustrates schematically one embodiment of the reaction that takes place in the CDAL 150 when analyte 80 is present in the particle 124 that combined with the CDAL 150. This figure is as in S. C. Hill, Aerosol Particle Analyzer for Measuring the Amount of Analyte in Airborne Particles, U.S. patent application Ser. No. 10/708,191. FIG. 2 shows how the fluorescence of the analysis liquid 800 changes, so that the fluorescence of the CDAL 150 varies with the amount of analyte 80 in the particles 124 that combined with the CDAL 150. The example shown in FIG. 2 is a variation of that shown in FIG. 6A of an article by R. L. Nutiu and Y. F. Li, "Structure-switching signaling aptamers," Journal of the American Chemical Society, 125, 4771–4778 (2003), (herein incorporated by reference, especially their FIG. 6A). In FIG. 2, the structure-switching signaling aptamer 820 is comprised of: (i) an aptamer (MAP) 822 chosen because it binds selectively to the analyte 80, (ii) a DNA oligonucleotide, Stem-2 824, which is covalently linked to the MAP 822; (iii) a DNA oligonucleotide, Stem-1 826 that is linked to Stem-2 824; (iv) a fluorophore (F) 828; (v) DNA oligonucleotide (FDNA) 830 that is linked to the fluorophore 828; (vi) a quencher (Q) 832; and (vii) a DNA oligonucleotide (QDNA) 834 that is linked to the quencher 832. The FDNA 830 forms the DNA duplex with Stem-2 824. The QDNA 834 forms the DNA duplex with Stem-1 826. In this structure-switching signaling aptamer 820, the fluorophore 828 and the quencher 832 are held near each other and the quencher 832 quenches the fluorescence of the fluorophor 828, so that the fluorescence of the fluorophor 828 is very significantly reduced. When analyte 80 is present in the CDAL 150, the MAP 822 of the structure switching signaling aptamer 820 binds to the analyte 80 as illustrated in FIG. 2, and its conformation changes. The FDNA 830 then no longer binds to Stem-2 824, and can diffuse away from the quencher 832, so that fluorophore 828 is no longer quenched, and can fluoresce brightly. The reaction illustrated in FIG. 2 differs from that shown in FIG. 6A of Nutiu and Li, in that the F 828 and Q 832 are interchanged so that the FDNA 830 diffuses relatively rapidly, even in cases where the analyte 80 has a very high molecular weight. That is, the FDNA 830 can diffuse throughout the CDAL 150 even if the analyte 80 is bound to the surface of the particle 124, and the particle 124 is too large to diffuse significantly. This ability of the fluorophore 828 to diffuse relatively rapidly throughout the CDAL 150 is important because without this ability, measurement of the amount of the fluorophore 828 that is unquenched can be much more difficult in the CDAL 150 than it would be in a flat cell. In the CDAL 150, the light that excites the fluorescence as well as the fluorescence emitted, is refracted at the curved surface of the CDAL 150, and this bending of the light makes the measurement of fluorescence from point sources inside a droplet problematical (see e.g., S. C. Hill, M. D. Barnes, N. Lermer, W. B. Whitten, and J. M. Ramsey, Simulation of single-molecule photocount statistics in microdroplets," Analytical Chemistry, 70, 2964–2971 (1998), herein incorporated by reference). If the fluorophore 828, when it is unquenched, is localized to a single particle 124 inside the CDAL 150, then even if a series of CDAL 150 all contain the same amount of unquenched fluorophore 828, then measurements of the fluorescence from those CDAL 150 have a large statistical variation and so the variation in the amount of analyte 80 in the CDAL 150 also appears to also have this large variation. Therefore, the measurement of the amount of analyte 80 is much less accurate than if the unquenched fluorophore 828 diffuses throughout the droplet. This is not to say that optical schemes for measuring the fluorescence from a single fluorescent-tagged particle 124 in a droplet could not be devised. They could be, but these would require illumination and collection of light from more angles, and that makes the overall design more complex, and more expensive.

For cases where the analyte 80 is an oligonucleotide, for example, a piece of RNA specific for some bacterium, the approach illustrated in FIG. 2 is used in one exemplar. For this case, the MAP 822 is replaced by a strand of oligonucleotide that is complementary to the analyte 80.

Referring again to FIG. 1, the APD 900 is as described by Richard Chang, Yong-Le Pan, Ronald Pinnick and Steven Hill, "Method and Instrumentation for Measuring Fluorescence Spectra of Individual Airborne Particles Sampled from Ambient Air," US 2004/0125371 A1, herein incorporated by reference. Further use of such a system is described by R. G. Pinnick, S. C. Hill, Y. Pan and R. K Chang, "Fluorescence spectra of atmospheric aerosol at Adelphi, Md., USA: measurement and classification of single particles containing organic carbon," Atmospheric Environment, 38, 1657–1672 (2004), herein incorporated by reference. Both of these descriptions include an air-to-air concentrator, which concentrates particles from a large volume of air into a smaller volume of air, so that the effective sample rate of the system is much larger. In some embodiments of the present invention, the APA 100 includes an air-to-air concentrator. An instrument that measures fluorescence of individual airborne particles and then sorts them based on their fluorescence spectra is described by Y. -L. Pan, V. Boutou, J. R. Bottiger, S. S. Zhang, J. -P. Wolf, and R. K. Chang, "A Puff of Air Sorts Bioaerosols for Pathogen Detection," Aerosol Science and Technology, 38, 598–602 (2004), herein incorporated by reference. In this paper, the detector for the fluorescence spectrum is especially suited for shooting CDAL 150 at selected particles 124 when the airflow rate is relatively high, because the fluorescence spectra can be read and analyzed relatively quickly.

Referring again to FIG. 1, the CDG 200 ejects a charged-droplet-of-the-analysis-liquid CDAL 150 when the CCSVES sends it a signal. In one embodiment, the CDG 200 is as described by S. Arnold, P. Hendrie and B. V. Bronk, U.S. Pat. No. 5,532,140, Method and Apparatus for Suspending Microparticles, column 4. A piezoelectric droplet generator, also employing induction charging, was used to inject droplets into a LQ by K. C. Ng, J. V. Ford, S. C. Jacobson, J. M. Ramsey, and M. D. Barnes, "Polymer microparticle arrays from electrodynamically focused microdroplet streams," Review of Scientific Instruments, 71, 2497–2499 (2000), and described by M. D. Barnes, US Patent Application 2004/0145085, Photonic Polymer-Blend Structures and Method for Making, both herein incorporated by reference. A microdroplets-on-demand-generator (MODG) is described by D. W. Noid, J. U. Otaigbe, M. D. Barnes, B. G. Sumpter, and C. -Y. Kung, Apparatus for and Method of Producing Monodisperse Submicron Polymer Powders from Solution, U.S. Pat. No. 6,461,546 B1, herein incorporated by reference. The company Microdrop, GmbH, sells a droplet generation system using a piezoelectric valve that that shoots particles at 2 m/s or 3 m/s. A solenoid valve, e.g., the VHS-LT sold by The Lee Company, Essex, Conn., along with induction charging, is used in some embodiments.

The approach of hitting the particle as it flies by is similar to that described for sorting airborne particles by hitting them with a puff of air as described by Y. -L. Pan, V. Boutou, J. R. Bottiger, S. S. Zhang, J. -P. Wolf, and R. K. Chang, "A Puff of Air Sorts Bioaerosols for Pathogen Detection," Aerosol Science and Technology, 38, 598–602 (2004), herein incorporated by reference. The difference from that prior work is that instead of hitting selected particles with a puff of air to change the particle's 124 trajectory, the particles 124 are hit with a CDAL 150 and combine with that CDAL 150 so that the analyte 80 in the particles can be measured, and so that the particle 124 collected into the CDAL 150 can be focused, levitated, and deposited into a small region, as desired.

Figure 3A:
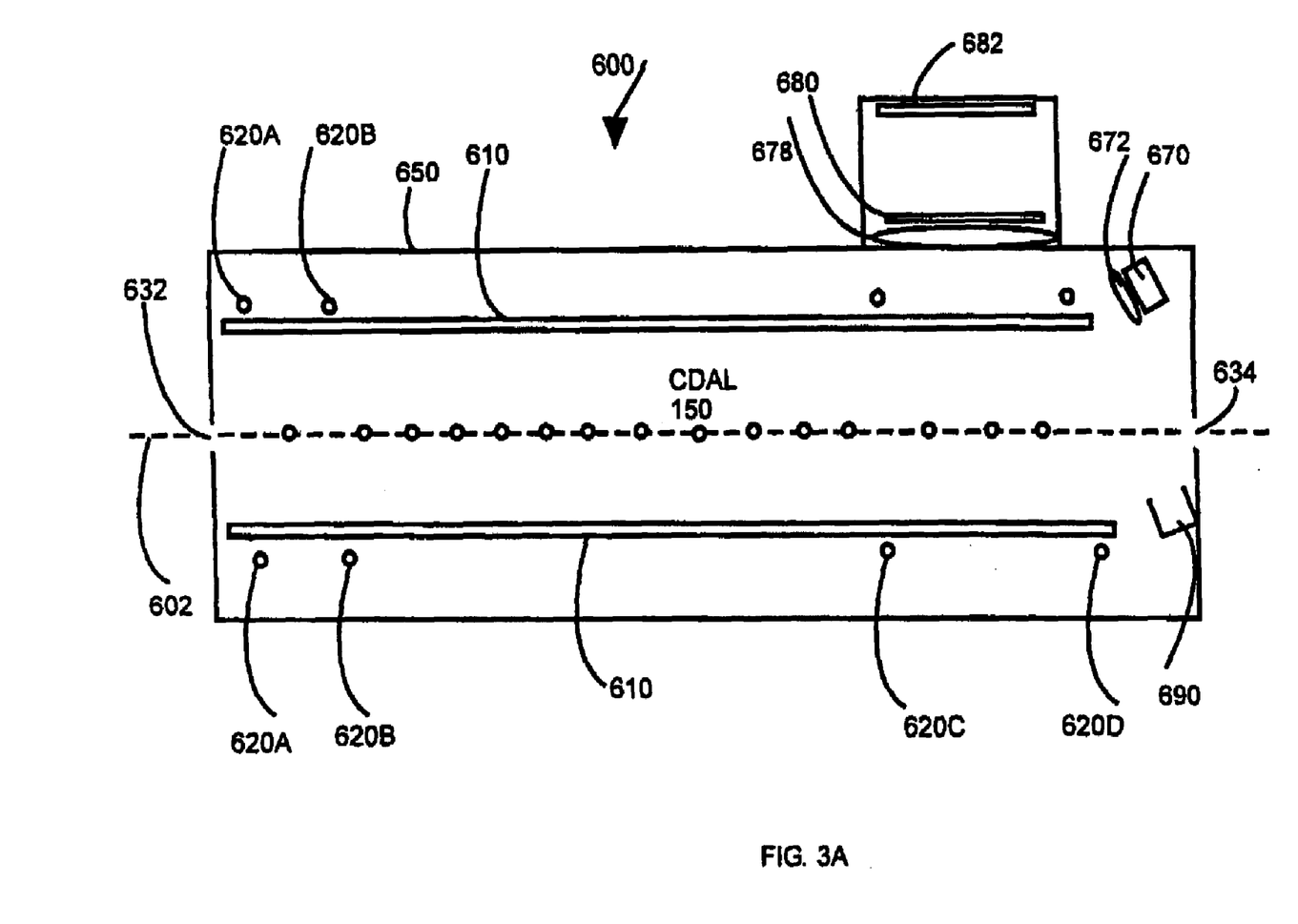
Figure 3B:
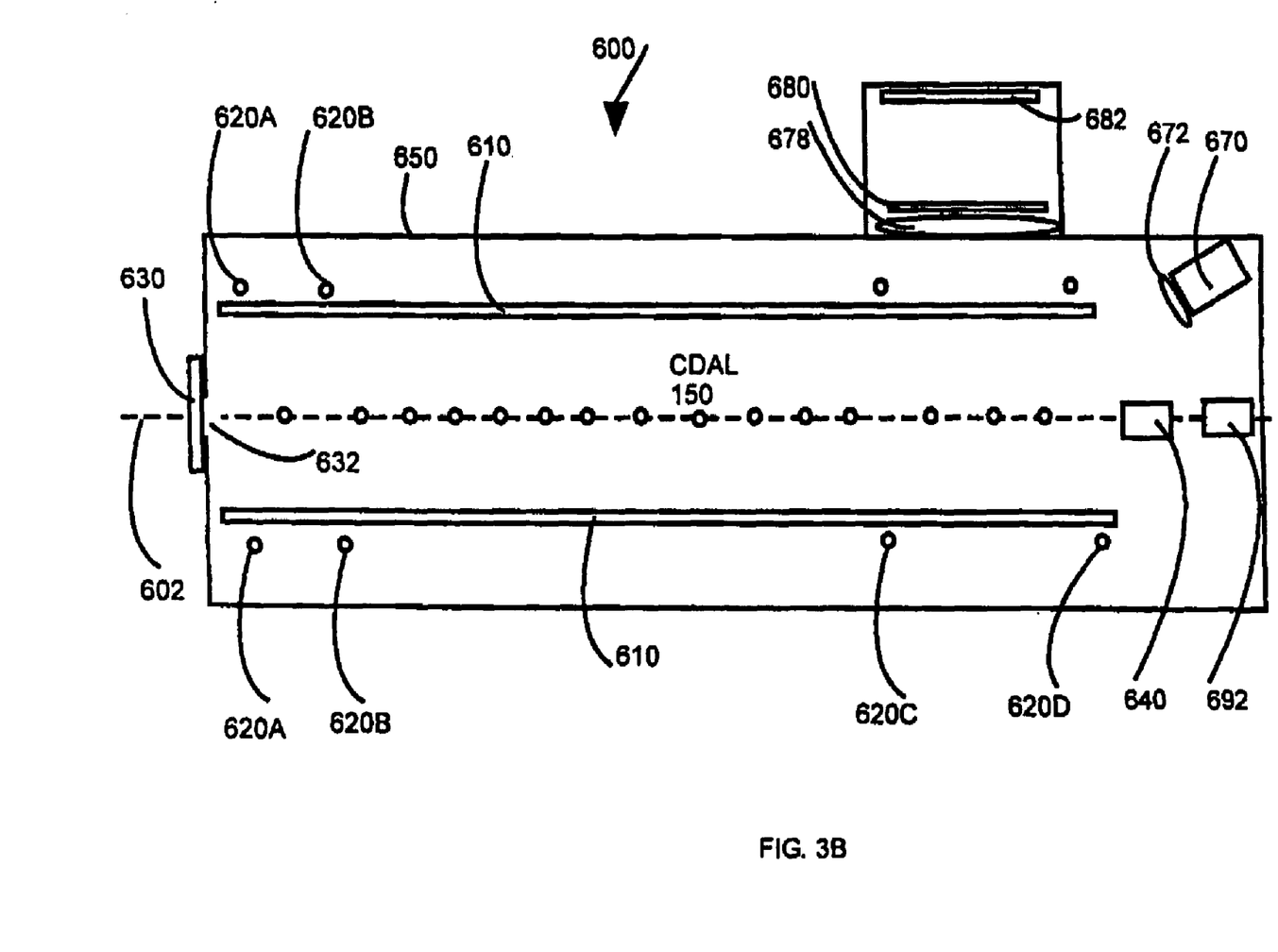

FIG. 3A illustrates schematically one embodiment of the DAS 600. This figure is similar to FIG. 4A in S. C. Hill, Aerosol Particle Analyzer for Measuring the Amount of Analyte in Airborne Particles, U.S. patent application Ser. No. 10/708,191. FIG. 3A includes components such as a linear quadrupole LQ 610; a multiplicity of DAS rings 620 that surround the LQ 610; and a DAS container 650. The DAS container 650 is substantially airtight except for a DAS input orifice 632 through which the CDAL 150 moves from the PDCS 400 into the DAS 600, and an output orifice 634 through which the CDAL 150 may be ejected so that it may be stored or analyzed further, using additional analyzers or storage devices, the specifics of which are outside the scope of this invention.

FIG. 3A also includes components such as a laser diode (LD) 670 to excite fluorescence in the CDAL 150, an LD-lens 672 to direct the emission from the LD 670 to at least one CDAL 150; a detector lens 678; a photodetector array 682 to detect the fluorescence; and a detector filter 680 to block the emission from the LD 670 from reaching the photodetector array 682.

Typically, multiple CDAL 150 are levitated between the second DAS ring 620B and the third DAS ring 620C, and these CDAL 150 are separated somewhat uniformly because they are uniformly charged and repulse one another. The holding region is the region between the second DAS ring 620B and the third DAS ring 620C. The measurement region is the region between the third and fourth DAS rings 620C and 620D.

In the embodiment described here the CDAL 150 is positively charged. Most of the time the potential applied to the first DSA ring 620A is positive so that CDAL 150 levitated near the LQ axis 602 are repulsed if they move toward the inlet. When a CDAL 150 is ejected from the PDCS 400 toward the DAS 600, the voltage of the first DAS ring 620A is lowered briefly so that the CDAL 150 can enter the DAS 600. That CDAL 150 is then held between the first DAS rings 620A and the second DAS ring 620B. Then the voltage of the first DAS ring 620A is raised while the voltage on the second DSA ring 620B is lowered, so that the CDAL 150 is pushed toward the measurement region, and the voltages of the third and fourth DAS rings 620C and 620D are also lowered so that the CDAL 150 in the holding region that is nearest the third DAS ring 620C enters the measurement region and the CDAL 150 nearest the fourth DAS ring 620D moves out of the measurement region and into a receptacle 690 where it is held, along with all the other CDAL that enter the receptacle 690 for possible further analysis.

In some embodiments the LQ is not exactly horizontally oriented, but is tilted so that particles 124 drift, because of gravity, from the input orifice 632 toward the output orifice 634. The height of the CDG 200 and the trajectory of the CDAL 150 ejected from the CDG 200 are adjusted so that the CDAL 150 enter the LQ 610 near the LQ axis 602 and in a direction parallel to this LQ axis 602. Having the CDAL 150 pulled by gravity toward the output orifice 634 can simplify the control of the CDAL 150 motion in the LQ 610.

The emission from the laser diode (LD) 670 is focused by the LD-lens 672, so that this emission somewhat uniformly illuminates the CDAL 150 in the measurement region and excites fluorescence in the CDAL 150. The detector filter 680 passes the fluorescence emission from the CDAL 150 and blocks the emission from the LD 670. The fluorescence emission from the CDAL 150 passes through the detector filter 680 and is imaged by the detector lens 678 onto the detector array. The CCVSE reads these fluorescence values from the photodetector array 682. In some embodiments there are as many measurements of the fluorescence of each CDAL 150 as there are CDAL 150 levitated in the measurement region at any time. These multiple measurements are used to ascertain time-dependent variations of the fluorescence measured which may occur if the reaction between the analyte 80 and the analysis liquid 800 is not essentially complete by the time the CDAL 150 reaches the measurement region, or if the fluorophore 828 has not diffused sufficiently so that the fluorescence of the CDAL 150 varies only little as the CDAL 150 rotates. In some embodiments there are additional regions for measuring the fluorescence of the particles, so that time-dependent variations of the fluorescence can be measured over a larger range of times.

FIG. 3B illustrates schematically another exemplar of the DAS 600, also similar to FIG. 4B in S. C. Hill, U.S. patent application 10/708191. In addition to the components of FIG. 3A, it includes deflection plates 640 and two receptacles 692 so that CDAL 150 ejected from the LQ 610 can be sorted by applying voltages to the deflection plates 640, in order to sort CDAL 150 having a greater fluorescence from those having a lesser fluorescence. This exemplar of the DAS 600 also includes a shutter 630 in front of the DAS orifice 632. This shutter 630 is closed most of the time, but is opened briefly when a CDAL 150 is ejected from the PDCS 400 into the DAS 600. This shutter helps to maintain the high humidity in the DAS 600. Also shown in FIG. 3B is a water level sensor that senses the level of water in the container, and a water pump that pumps a small amount of water into the bottom of the container when the water level drops below the required level, so as to keep the humidity in the chamber high enough that the evaporation of the CDAL 150 is not rapid.

In another embodiment, the APA 100 of FIGS. 1, 3A, and 3B is rotated so that the particles 124 are drawn into the APA 100 on a substantially horizontal trajectory and the CDG 150 moves in a substantially downward trajectory toward the particle 124, after it has combined with the particle 124, and as it moves into the DAS 600 and through the LQ 610. In this case the CDAL 150 are not levitated by the LQ 610, but the LQ 610 acts as a guide to focus the droplets to the LQ axis 602 so that the CDAL 150 when it exits the DAS 600 can be deposited with high positional accurately either: (a) onto a surface for storage or further analysis, (b) into a well of an array of microtiter wells, where they can be further analyzed, or (c) into the input port of an additional analyzer, such as microfluidic bioanalyzer, which can perform a further analysis. K. C. Ng, J. V. Ford, S. C. Jacobson, J. M. Ramsey, and M. D. Barnes, "Polymer microparticle arrays from electrodynamically focused microdroplet streams," Review of Scientific Instruments, 71, 2497–2499 (2000), herein incorporated by reference, showed that by using a linear quadrupole to focus charged droplets and using a computer controlled x-y stage to move their collection surface, they were able to deposit particles with a positional accuracy of about 2 micrometers. The surface for storage, array of microtiter wells, and the additional analyzer are outside the scope of this invention, but are mentioned to clarify why there is an advantage in using the LQ 610 to guide the particles. When the airborne particles 124 are focused by the LQ 610 and positioned very accurately onto a surface, the density of stored particles per area of surface can be large and the microtiter well volumes could be very small. When the airborne particles 124 are focused by the LQ 610 and positioned accurately into the input to a microfluidic analyzer for biological or chemical analytes 80, the amount of reagents required for the analysis in the microdluidic device can be limited by the intrinsic limitations of the microfluidic device, not by the problems of extracting the particle 124 from the gas 120 and depositing them in the analyzer. A recent example of a microfluidic system for analyzing cells and other particles, along with references to similar work, is described by C. R. Paulsen, C. T. Culbertson, S. C. Jacobson, and J. M. Ramsey, "Static and Dynamic Acute Cytotoxicity Assays on Microfluidic Devices," Analytical Chemistry, 77, 667–672 (2005), herein incorporated by reference.

Although the levitator that is described and emphasized here is a linear quadrupole, acoustic levitation can also be used for holding and examining particles, as described by S. Holler, M. Surbek, R. K. Chang, and Y. L. Pan, "Two-dimensional angular optical scattering patterns as droplets evolve into clusters," Optics Letters, 24, 1185–1187 (1999), herein incorporated by reference.

Although only the measurement of the fluorescence intensity is described here in detail, other fluorescence properties such as the fluorescence polarization, the fluorescence spectrum, and the fluorescence lifetime can also be used in some embodiments of the APA 100, and methods for measuring these properties are well enough known, that more does not need to be stated here. Also, methods for measuring other optical properties such as the light scattering properties of intensity, polarization, spectral intensity, and angular-dependent intensity have been described by many researchers.

Figure 4:
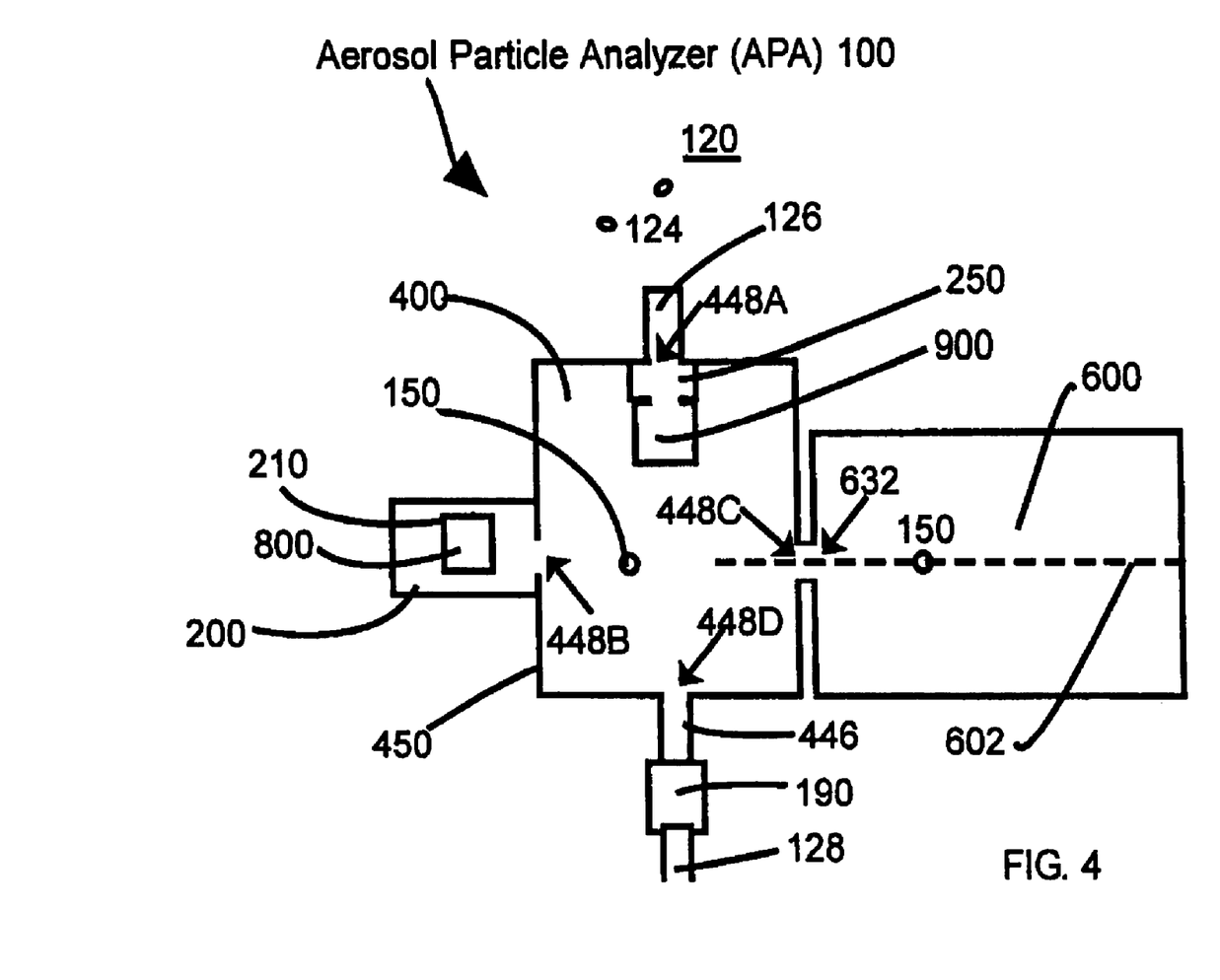
FIG. 4 illustrates schematically an APA that includes a charger.

In some embodiments, a charger 250, which imparts a charge to the particles 124 drawn through it, is in the PDCS 400 between the inlet and the APD 900, as illustrated in FIG. 4. In a preferred embodiment, particles 124 exiting the charger 250 are negatively charged and the CDAL 150 is positively charged. In one embodiment the charger 250 is of the corona-discharge type as described by R. Vehring, C. L. Aardahl, G. Schweiger and E. J. Davis, "The characterization of fine particles originating from an uncharged aerosol: size dependence and detection limits for Raman analysis," Journal of Aerosol Science, 29, 1045–1061 (1998), especially pp. 1048–1050, and p. 1057, and by C. L. Aardahl, et al., Electrodynamic trapping of aerocolloidal particles: experimental and theoretical trapping limits," Journal of Colloid and Interface Science, 192, 228–237 (1997), both herein incorporated by reference, especially pp. 231–233. In another preferred embodiment, alternating-current corona charging is used to impart more charge per particle 124 with fewer particles 124 lost, as described by M. Lakowski, "Unipolar charging of aerosol particles in alternating electric field," Journal of Electrostatics, 51–52, 225–231 (2001), especially FIG. 2 on page 228 of that paper and the description of the apparatus on p. 227 and 228, both of which are herein incorporated by reference. In another embodiment the charger employs an ultraviolet light source for charging using the photoelectric effect. C. L. Aardahl, et al., Electrodynamic trapping of aerocolloidal particles: experimental and theoretical trapping limits," Journal of Colloid and Interface Science, 192, 228–237 (1997), described charging using the photoelectric effect. In another embodiment the particles are charged using a radioactive source as is used by TSI Inc., in their Scanning Mobility Particle Sizer.

In a simple embodiment of the APA 100, suitable for particles 124 and analytes 80 that react very rapidly with the analysis liquid 800, the DAS 600 does not employ a LQ 610, but instead detects the fluorescence quickly after the CDAL enters the DAS 600. In such a case, the CDAL does not need to be charged, and so the voltage used to impart a charge to the CDAL 150 leaving the charger 200 can be turned off, and the CDAL 150 could be termed a droplet of the analysis liquid. An example of a reaction that could be sufficiently rapid is that between particles 124 composed of a mixture of sulfuric acid and water, and a CDAL 150 composed of water and a pH-sensitive fluorescent dye. Such a reaction could be used in measuring the acid content droplets. Or, for example, if the particle 124 is a micropdroplet of water, possibly a fog droplet, that contains several bacteria, and if in the CDAL 150 there is a sufficient concentration of the structure switching signaling aptamer 820 that binds to molecules on the surface of that type of bacteria, then the development of the fluorescence in the CDAL 150 after it has combined with the particle 124 may be very rapid, and the fact that multiple copies of the bacteria are in the CDAL 150 makes it less likely that the fluorescence would not be detected, even if there were very little time for the fluorophores to diffuse throughout the droplet.

Although various preferred embodiments of the present invention have been described herein in detail to provide for complete and clear disclosure, it will be appreciated by those skilled in the art that variations may be made thereto without departing from the spirit of the invention or the scope of the appended claims.

We claim:

1. An aerosol-particle analyzer (APA) for measuring the amount of an analyte in particles in a gas comprising:
    (a) an analysis liquid chosen to be suitable for collecting particles for further analysis;
    (b) a droplet generator, having a droplet generator output, that generates a droplet of the analysis liquid (DAL) and ejects it out of said droplet generator output when signaled to do so;
    (c) a particle-droplet-collision subsystem (PDCS) consisting of an aerosol particle detector enclosed in a gas-tight container, having a droplet input connected to the droplet generator output, a particle input, a PDCS-DAL output, and a vacuum connection that:
        (i) accepts the gas containing the particles via the particle input;
        (ii) detects when particles in the gas that are moving toward a particle-droplet collision region and signals for the droplet generator to eject a DAL toward the particle-droplet collision region;

(iii) accepts the DAL via the droplet input so that the DAL moves through the particle-droplet collection region and collides with the particle that was detected, and combines with the particle; and (iv) passes the DAL that has combined with the particle out of the PDCS through PDCS-DAL output;

(d) a vacuum pump connected to the PDCS vacuum connection that draws the gas and particles into the PDCS, where the gas and any particles not combined with the DAL are then evacuated;

(e) a droplet analysis system that accepts the DAL ejected from the PDCS through a vacuum tight connection and measures the amount of analyte in the CDAL.

2. An aerosol-particle analyzer (APA) for measuring the amount of an analyte in particles in a gas according to claim 1 comprising:

(a) an analysis liquid chosen such that when the analysis liquid is mixed with the particles, an optical property of the analysis liquid varies according to the amount of the analyte in the particles;

(b) a charged droplet generator, having a charged-droplet generator output, that generates a charged droplet of the analysis liquid (CDAL) and ejects it out of said charged-droplet generator output when signaled to do so;

(c) a particle-droplet-collision subsystem (PDCS) consisting of an aerosol particle detector enclosed in a gas-tight container, having a charged-droplet input connected to the charged-droplet generator output, a particle input, a PDCS CDAL output, and a vacuum connection that:

(i) accepts the gas containing the particles via the particle input;

(ii) detects when particles in the gas that are moving toward a particle-droplet collision region and signals for the charged droplet generator to eject a CDAL toward the particle-droplet collision region;

(iii) accepts the CDAL via the charged-droplet input so that the CDAL moves through the particle-droplet collection region and collides with the particle that was detected, and combines with the particle; and (iv) passes the CDAL that has combined with the particle out of the PDCS through PDCS CDAL output;

(d) a vacuum pump connected to the PDCS vacuum connection that draws the gas and particles into the PDCS, where the gas and any particles not combined with the CDAL are then evacuated;

(e) a droplet analysis subsystem (DAS), having a DAS input orifice for accepting the CDAL that has combined with the particles consisting of:

(i) an electrodynamic levitator that levitates the CDAL that has combined with the particles ejected by the PDCS and holds them while the reaction between the CDAL and the analyte occurs;

(ii) a means to control the motion of the CDAL in the electrodynamic levitator;

(iii) a container that surrounds the levitated CDAL and that is substantially airtight, except for the DAS input orifice through which the CDAL enter and a DAS output orifice through which the CDAL may pass after they are analyzed, where the container is substantially airtight so that the CDAL does not evaporate quickly, and so that air currents do not push the CDAL out of the electrodynamic levitator;

(iv) a means to detect changes in the optical property of the levitated CDAL, so that the amount of analyte in the CDAL, and therefore in the particles that combined with the CDAL, can be determined from these measurements of the optical property.

3. The APA of claim 2 wherein the optical property is a fluorescence property chosen from a group consisting of the fluorescence intensity, the fluorescence polarization, the fluorescence spectrum, and the fluorescence lifetime.

4. The APA of claim 2 wherein the optical property is a light scattering property chosen from a group consisting of the intensity, polarization, spectral intensity, and angular-dependent intensity.

5. The APA of claim 2 wherein the analysis liquid is a water solution that contains sensor molecules that selectively binds to the analyte.

6. The APA of claim 5 wherein the sensor molecule is protein.

7. The APA of claim 5 wherein the sensor molecule is an aptamer.

8. The APA of claim 5 wherein the sensor molecule is phage-displayed epitope.

9. The APA of claim 5 wherein the sensor molecule is a nucleic acid.

10. The APA of claim 1 wherein a charger in the PDCS imparts a charge to the particles drawn into the PDCS, where the polarity of the charge is opposite to that of the CDAL.

11. The APA of claim 10 wherein the charger generates a corona discharge.

12. The APA of claim 11 wherein the charger is of the alternating-current corona charging type.

13. The APA of claim 1 wherein the electrodynamic levitator of the DAS is a linear quadrupole.

14. The APA of claim 1 wherein said DAS further includes a receptacle to collect and store the CDAL after the optical property of the CDAL has been measured so that such collected CDAL can be further analyzed.

15. The APA of claim 1 wherein said DAS further includes a multiplicity of receptacles and a means to sort the CDAL into different receptacles according to the measured value of the optical property.

16. The APA of claim 1 wherein said DAS further includes an exit port so that CDAL can be ejected from the DAS into another instrument for further analysis.

17. The APA of claim 1 wherein said DAS further includes a shutter that is open when the CDAL is injected into the DAS, and is closed otherwise, so that the rate that water vapor leaves the DAS through the orifice is reduced, so that the humidity in the DAS remains high.

18. The APA of claim 1 further including an aerosol particle concentrator connected to PDCS which concentrates the particles before they enter the PDCS so that the APA is sensitive to particles which contain lower concentrations of analyte and to lower concentrations of particles that contain the analyte.

19. The APA of claim 1 further including a nozzle connected to the output of the aerosol particle concentrator, where said nozzle is positioned inside a sheath-flow tube so that the particles concentrated by the aerosol particle concentrator are kept from dispersing so that a higher fraction of these particles can collide with one the CDAL and be analyzed in the DAS.

20. The APA of claim 1 wherein said aerosol particle detector has a means to measure the size, at least approximately by using calibration data, of each particle it detects so that the size of the particle that combines with the CDAL is known approximately, so that the concentration of the analyte in the particle can be estimated, and so that the strength of any background or nonspecific-binding signals measured from the CDAL can be estimated, at least from calibration particles, and so that the charged droplet generator need only shoot CDAL at particles in a preselected size range.

21. The APA of claim 1 wherein said aerosol particle detector has a means to measure the laser-induced fluorescence spectrum of each particle it detects so that the content of certain biomolecules such as tryptophan in each particle that combines with the CDAL can be estimated, so that the strength of any background or nonspecific-binding signals measured from the CDAL can be more accurately estimated, at least from calibration particles, and so that the charged droplet generator need only shoot CDAL at particles having preselected laser-induced fluorescence properties.

22. The APA of claim 1 wherein the analysis liquid further contains an additional sensor molecule that selectively binds to an additional region of the analyte.

23. The APA of claim 22 wherein when the additional sensor molecule binds to the additional region of the analyte, the fluorescence of an additional fluorophore changes, and wherein the spectral peak of the fluorescence emission that changes when the sensor molecule binds to the analyte is different from the spectral peak of the fluorescence emission that changes when the additional sensor molecule binds to the additional region of the analyte.

24. The APA of claim 1 wherein the analysis liquid further contains an additional sensor molecule that selectively binds to an additional analyte.

25. The APA of claim 24 wherein, when the additional sensor molecule binds to the additional analyte, the fluorescence of an additional fluorophore changes, and wherein the spectral peak of the fluorescence emission that changes when the sensor molecule binds to the analyte is different from the spectral peak of the fluorescence emission that changes when the additional sensor molecule binds to the additional analyte.

26. The APA of claim 1 wherein said DAS further includes a means to measure multiple optical properties of one CDAL.

27. The APA of claim 1 wherein said DAS further includes a region in the container to hold water that can evaporate to keep the humidity in the DAS high.

28. The APA of claim 1 wherein said DAS further includes a means to detect the water level in the region in the container that holds the water, and a means to inject water into the region in the container that holds the water if this water level drops below some level.

* * * * *